United States Patent [19]
Bueschken et al.

[11] Patent Number: 5,831,135
[45] Date of Patent: Nov. 3, 1998

[54] PROCESS FOR THE CATALYTIC SELECTIVE HYDROGENATION OF POLYUNSATURATED ORGANIC SUBSTANCES

[75] Inventors: Wilfried Bueschken, Haltern; Juergen Hummel, Marl, both of Germany

[73] Assignee: Huels Aktiengesellschaft, Marl, Germany

[ * ] Notice: The term of this patent shall not extend beyond the expiration date of Pat. No. 5,675,045.

[21] Appl. No.: 944,433

[22] Filed: Oct. 6, 1997

Related U.S. Application Data

[63] Continuation of Ser. No. 668,357, Jun. 26, 1996, Pat. No. 5,675,045.

[30] Foreign Application Priority Data

Jul. 8, 1995 [DE] Germany ................. 195 24 971.2

[51] Int. Cl.⁶ .................................................. C07C 29/14
[52] U.S. Cl. .................. 568/881; 568/883; 568/420; 568/458; 582/259; 582/260
[58] Field of Search ................... 568/881, 883, 568/420, 458; 585/259, 280

[56] References Cited

FOREIGN PATENT DOCUMENTS

| | | |
|---|---|---|
| 0 011906 | 6/1980 | European Pat. Off. . |
| 0 541 871 | 5/1993 | European Pat. Off. . |
| 781 405 | 8/1957 | United Kingdom . |
| 1 032 838 | 6/1966 | United Kingdom . |
| 87 07598 | 12/1987 | WIPO . |

*Primary Examiner*—Gary Geist
*Assistant Examiner*—Sreeni Padmanabhan
*Attorney, Agent, or Firm*—Oblon, Spivak, McClelland, Maier & Neustadt, P.C.

[57] ABSTRACT

The present invention relates to a process for the catalytic selective hydrogenation of a polyunsaturated organic compound, wherein the hydrogenation is carried out in a plurality of two or more series-connected loops, wherein each loop involves the use of one reactor, which comprises:

(a) feeding the polyunsaturated organic compound and hydrogen to an upper part of a reactor to catalytically hydrogenate said the polyunsaturated organic compound to produce a hydrogenation product, (b) recycling a portion of said hydrogenation product back into said upper part of said reactor, (c) feeding the remainder of said hydrogenation product from said reactor to an upper part of a subsequent reactor wherein the polyunsaturated organic compound is catalytically hydrogenated to produce a subsequent hydrogenation product, and wherein a portion of said subsequent hydrogenation product has been recycled and is fed with said remainder of said hydrogenation product to said upper part of said subsequent reactor, (d) repeating step (c) until the subsequent reactor is the last reactor, (e) recovering the remainder of said subsequent hydrogenation product from said last reactor, and (f) obtaining the desired compound(s) from the product of step (e).

20 Claims, 1 Drawing Sheet

PROCESS FOR THE CATALYTIC SELECTIVE HYDROGENATION OF POLYUNSATURATED ORGANIC SUBSTANCES

This is a Continuation of application Ser. No. 08/668,357 filed on Jun. 26, 1996, now U.S. Pat. No. 5,675,045.

BACKGROUND OF THE INVENTION

1. Field of the Invention

The present invention relates to a process for the catalytic selective hydrogenation of polyunsaturated organic substances.

2. Description of the Background

A number of important organic compounds are obtainable, starting from polyunsaturated organic substances, by processes for catalytic selective hydrogenation. The aim of selective hydrogenation is generally to obtain the desired hydrogenation product in the highest possible purity with the highest possible yield.

The exclusive preparation of a compound of the type B by hydrogenating an unsaturated compound of the type A is made more difficult by the fact that the target compound (type B) can react further to give a compound of the type C.

| A | $\xrightarrow{K_1}$ | B | $\xrightarrow{K_2}$ | C |
|---|---|---|---|---|
| Polyunsaturated compound | | Partially hydrogenated compound | | Polyhydrogenated compound |

For continuous selective hydrogenation in the liquid phase, the following types of process are known:

(I) the hydrogenation is carried out in a single stage in a so-called loop. This achieves good thermal control and a short residence time on the catalyst.

(II) the hydrogenation is carried out in two stages, in the loop in the first stage and in straight flow-through in the second stage.

The disadvantage of the first procedure is that complete conversion of A is not achieved. This means a loss of yield and, if B is to be isolated, a considerable expense for product separation.

In the second procedure, A is completely hydrogenated. However, it is a disadvantage that overhydrogenation to give C also occurs. This likewise means a loss in yield and product separation.

The object was therefore to provide a process which enables polyunsaturated compounds to be catalytically selectively hydrogenated in an economical manner.

SUMMARY OF THE INVENTION

It has now surprisingly been found that virtually complete conversion with simultaneously high selectivity is achievable if a plurality, i.e. at least two, loops connected in series is operated.

DESCRIPTION OF THE PREFERRED EMBODIMENTS

Figure 1:
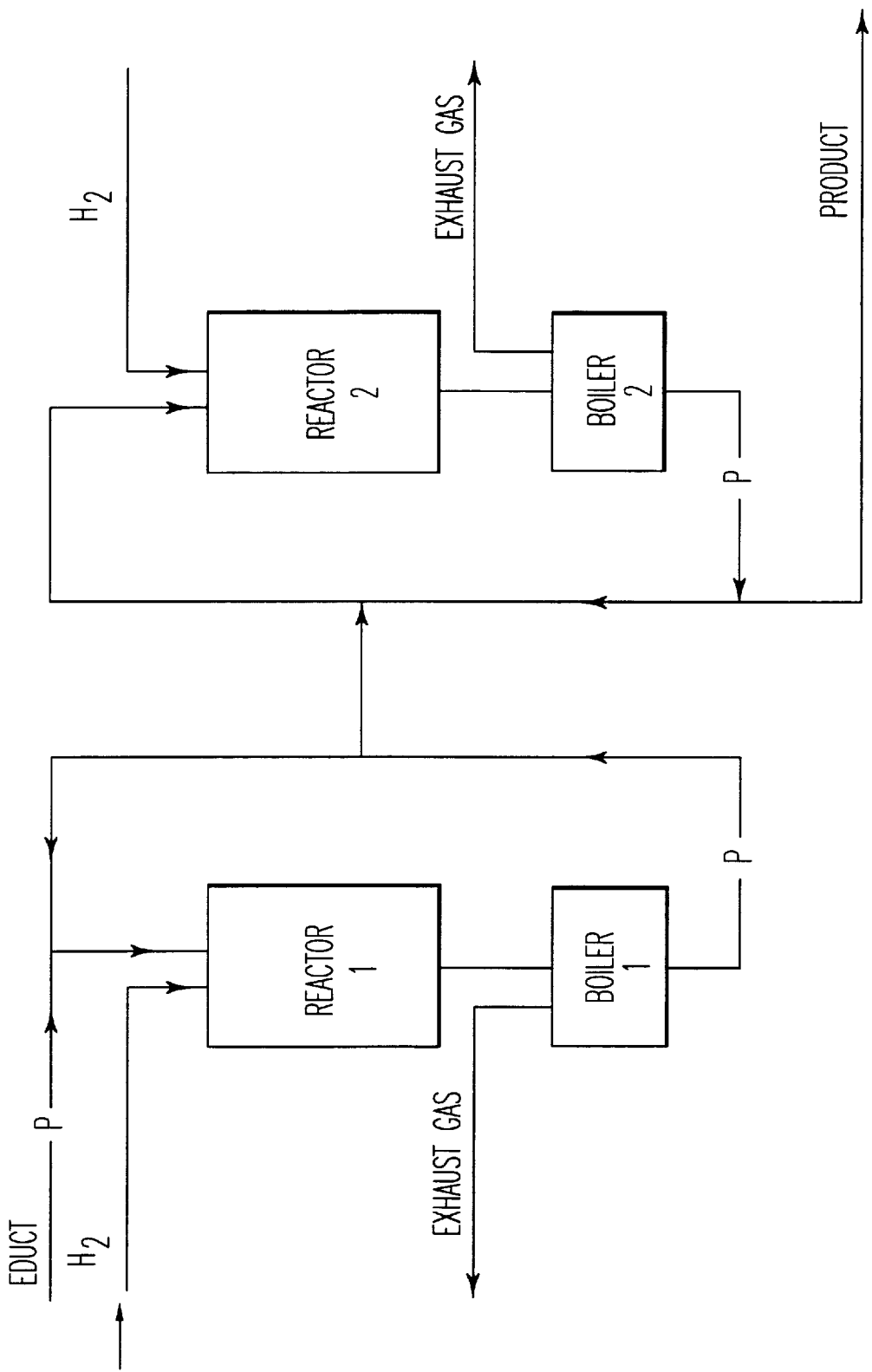
FIG. 1 shows the diagram of a double loop procedure. In this procedure, the starting material A is fed into a portion of the hydrogenation discharge of the first reactor and this mixture is passed to the top of the first reactor. Hydrogenation product is passed under level control from the hydrogenation reservoir of the first reactor into the loop of the second reactor. This mixture flows to the top of the second reactor. The end product is removed under level control from the hydrogenation reservoir of the second reactor. In the present process, the flow in the reactors can be turbulent or laminar.

The present process has the advantages below in comparison with the conventional, above-mentioned procedure (II) (1st stage loop: 2nd stage straight flow-through):

1. with the same amount of catalyst (sum of the amounts in the two reactors), the production rate is up to 90% higher.
2. the selectivity (less overhydrogenated product) is improved. At conversion rates of 99.9% and above, selectivities of over 99% are achieved.

The present invention therefore relates to a process for the catalytic selective hydrogenation of a polyunsaturated organic compound, wherein the hydrogenation is carried out in a plurality of two or more series-connected loops, wherein each loop involves the use of one reactor, which comprises:

(a) feeding the polyunsaturated organic compound and hydrogen to an upper part of a reactor to catalytically hydrogenate said polyunsaturated organic compound to produce a hydrogenation product, (b) recycling a portion of said hydrogenation product back into said upper part of said reactor, (c) feeding the remainder of said hydrogenation product from said reactor to an upper part of a subsequent reactor wherein the polyunsaturated organic compound is catalytically hydrogenated to produce a subsequent hydrogenation product, and wherein a portion of said subsequent hydrogenation product has been recycled and is fed with said remainder of said hydrogenation product to said upper part of said subsequent reactor, (d) repeating step (c) until the subsequent reactor is the last reactor, (e) recovering the remainder of said subsequent hydrogenation product from said last reactor, and (f) obtaining the desired compound(s) from the product of step (e).

In the process of the invention, the hydrogenation is preferably carried out in two series-connected loops; the polyunsaturated organic substances, together with some of the hydrogenation product from the 1st reactor, being passed to the top of the 1st reactor, the remainder of the hydrogenation product from the 1st reactor, together with some of the hydrogenation product from the 2nd reactor, being passed to the top of the 2nd reactor and the end product being obtained from the remainder of the hydrogenation product from the 2nd reactor.

The process of the invention can generally be carried out in a temperature range between 0° and 200° C. and at a pressure of 1 to 200 bar, the hydrogenation conditions being dependent on the starting material and the desired hydrogenation product. The flow in the reactor can be laminar or turbulent. In the process of the invention, hydrogenation is preferably carried out in the liquid phase in all reactors. The catalysts used in the process of the invention can generally be commercial hydrogenation catalysts, for example 0.5% $Pd/Al_2O_3$ (Engelhard).

Suitable starting materials are generally those polyunsaturated substances in which the partially hydrogenated compound B is less readily hydrogenated than the starting compound A. In particular, the process of the invention is advantageous for the preparation of the following classes of compounds:

a) preparation of olefins from acetylenes
b) preparation of olefins having at least one isolated double bond from conjugated olefins
c) preparation of saturated ketones from unsaturated ketones
d) preparation of saturated nitrites from unsaturated nitrites In the process of the invention, in particular, acetylenes can be selectively hydrogenated to form olefins and, in the case of olefins having conjugated double bonds, at least one of the conjugated double bonds is preferentially selectively hydrogenated, with retention of at least one unconjugated double bond.

In the case of organic substances having at least one multiple bond between two carbon atoms and at least one multiple bond between a carbon atom and a heteroatom, one or more multiple bonds between two carbon atoms are suitably selectively hydrogenated in the process of the invention, also with retention of the multiple bonds between a carbon atom and a heteroatom.

In addition, in the process of the invention, unsaturated ketones can be selectively hydrogenated to form saturated ketones, unsaturated aldehydes can be selectively hydrogenated to form saturated aldehydes, for example 3-propylhept-2-enal can be selectively hydrogenated to form 3-propylheptanal, but unsaturated nitrites can also be selectively hydrogenated to form saturated nitriles, and aldol condensation products of aldehydes prepared by hydroformylation can be selectively hydrogenated to form saturated aldehydes; however, the process of the invention not being intended to be restricted to the above-mentioned examples.

By means of the process of the invention, it is possible to prepare a number of unsaturated compounds with high selectivity and outstanding yield in a simple and economical manner by a catalytic hydrogenation of polyunsaturated organic substances.

The disclosure of German patent application 195 24 971.2, filed Jul. 8, 1995, is hereby incorporated by reference.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A process for the catalytic selective hydrogenation of a polyunsaturated organic compound to form one or more hydrogenated compounds, wherein the hydrogenation is carried out in a plurality of two or more series-connected loops, wherein each loop involves the use of one reactor, which comprises:

(a) feeding the polyunsaturated organic compound and hydrogen to an upper part of a reactor to catalytically hydrogenate said polyunsaturated organic compound to produce a hydrogenation product,
(b) recycling a portion of said hydrogenation product back into said upper part of said reactor,
(c) feeding the remainder of said hydrogenation product from said reactor to an upper part of a subsequent reactor wherein the polyunsaturated organic compound is catalytically hydrogenated to produce a subsequent hydrogenation product, and wherein a portion of said subsequent hydrogenation product has been recycled and is fed with said remainder of said hydrogenation product to said upper part of said subsequent reactor,
(d) repeating step (c) until the subsequent reactor is the last reactor, such that recycle is also carried out in the last reactor,
(e) recovering the remainder of said subsequent hydrogenation product from said last reactor, and
(f) obtaining from the product of step (e) one or more hydrogenated compounds.

2. A process as claimed in claim 1, wherein the hydrogenation is carried out in two series-connected loops.

3. A process as claimed in claim 1, wherein hydrogenation is carried out in the liquid phase in all reactors.

4. A process as claimed in claim 2, wherein hydrogenation is carried out in the liquid phase in all reactors.

5. A process as claimed in claim 1, wherein the flow is laminar in the reactor.

6. A process as claimed in claim 2, wherein the flow is laminar in the reactor.

7. A process as claimed in claim 3, wherein the flow is laminar in the reactor.

8. A process as claimed in claim 1, wherein the flow is turbulent in the reactor.

9. A process as claimed in claim 2, wherein the flow is turbulent in the reactor.

10. A process as claimed in claim 3, wherein the flow is turbulent in the reactor.

11. A process as claimed in claim 1, wherein the polyunsaturated compound is an acetylene which is selectively hydrogenated to form an olefin.

12. A process as claimed in claim 1, wherein the polyunsaturated compound is an olefin having conjugated double bonds, and wherein at least one of the conjugated double bonds of said polyunsaturated compound is selectively hydrogenated with retention of at least one unconjugated double bond.

13. A process as claimed in claim 1, wherein the polyunsaturated compound has at least one multiple bond between a carbon atom and a heteroatom, and one or more multiple bonds between two carbon atoms, and wherein said polyunsaturated compound is selectively hydrogenated with retention of the multiple bonds between carbon atoms and heteroatoms.

14. A process as claimed in claim 13, wherein unsaturated ketones are selectively hydrogenated to form saturated ketones.

15. A process as claimed in claim 13, wherein unsaturated aldehydes are selectively hydrogenated to form saturated aldehydes.

16. A process as claimed in claim 15, wherein aldol condensation products of aldehydes prepared by hydroformylation are selectively hydrogenated to form saturated aldehydes.

17. A process as claimed in claim 16, wherein 3-propylhept-2-enal is selectively hydrogenated to form 3-propylheptanal.

18. A process as claimed in claim 13, wherein unsaturated nitrites are selectively hydrogenated to form saturated nitriles.

19. A process as claimed in claim 1, wherein the selective hydrogenation is carried out at a temperature of 0° to 200° C.

20. A process as claimed in claim 1, wherein the selective hydrogenation is carried out at pressures of 1 to 200 bar.

* * * * *